(12) United States Patent
Ogaki et al.

(10) Patent No.: US 7,009,080 B2
(45) Date of Patent: Mar. 7, 2006

(54) PROCESS FOR PRODUCING HALOGENATED AROMATIC AMINE COMPOUND

(75) Inventors: Harunobu Ogaki, Shizuoka (JP); Takakazu Tanaka, Shizuoka (JP); Itaru Takaya, Kanagawa (JP); Yuka Ishiduka, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 219 days.

(21) Appl. No.: 10/671,674

(22) Filed: Sep. 29, 2003

(65) Prior Publication Data

US 2004/0127716 A1 Jul. 1, 2004

(30) Foreign Application Priority Data

Oct. 3, 2002 (JP) .............................. 2002-291282
Sep. 19, 2003 (JP) .............................. 2003-328076

(51) Int. Cl.
*C07C 209/10* (2006.01)
(52) U.S. Cl. ...................................... 564/307
(58) Field of Classification Search ................ 564/307, 564/308
See application file for complete search history.

(56) References Cited

U.S. PATENT DOCUMENTS 5,739,169 A * 4/1998 Ocain et al. ................. 514/658
6,034,206 A 3/2000 Yamamoto et al. .......... 528/397

FOREIGN PATENT DOCUMENTS

JP 11-21349 1/1999
JP 11-322679 11/1999
WO WO 01/55087 A1 8/2001

OTHER PUBLICATIONS

Janis Louie et al., "Palladium-Catalyzed Synthesis of Amines from Aryl Halides. Mechanistic Studies Lead to Coupling in the Absence of Tin Reagents," 36 (21) *Tetrahedron Lett.* 3609-3612 (1995).
David W. Old et al., "A Highly Active Catalyst for Palladium-Catalyzed Cross-Coupling Reactions: Room-Temperature Suzuki Coupling and Animation of Unactivated Aryl Chlorides," 120 *Am. J. Chem. Soc.* 9722-9723 (1998).
John P. Wolfe et al., "Palladium-Catalyzed Amination of Aryl Iodides," 61 *J. Org. Chem.* 1133-1135 (1996).

* cited by examiner

*Primary Examiner*—Brian Davis
(74) *Attorney, Agent, or Firm*—Fitzpatrick, Cella, Harper & Scinto

(57) ABSTRACT

A process for producing a halogenated aromatic amine compound by allowing an aromatic amine compound to react with a dihalogenated aromatic compound in the presence of i) a metallic catalyst having a phosphorus-containing ligand having at least one cyclic hydrocarbon group and ii) a basic compound in a non-reactive solvent.

10 Claims, No Drawings

US 7,009,080 B2

PROCESS FOR PRODUCING HALOGENATED AROMATIC AMINE COMPOUND

BACKGROUND OF THE INVENTION

1. Field of the Invention

This invention relates to a process for producing a halogenated aromatic amine compound.

2. Related Background Art

Halogenated aromatic amine compounds are useful compounds as intermediates of pharmaceuticals and agricultural chemicals, intermediates of coloring matters such as organic dyes and pigments, and also intermediates of organoelectroluminescence materials, and intermediates of photosensitive materials or organic conductor materials of organic photosensitive members in electrophotography.

In synthesizing halogenated aromatic amine compounds by conventional processes, they have been synthesized by, e.g., in the case of aminobiphenyl compounds, the reaction in which an aminobiphenyl compound is directly halogenated, or the Ullmann reaction in which a dihalogenated biphenyl compound and an amine compound are heated at a high temperature in the presence of a copper reagent (DAIYUHKI KAGAKU (Grand Organic Chemistry), Vol. 16, 52(1959), Asakura Shoten; YUHKIKAGAKU KOZA (Organic-Chemistry Course) 3, 66 (1983). However, in the reaction in which an aminobiphenyl compound is directly halogenated, an isomer different in halogen substitution position is present, and hence the desired compound can not efficiently be obtained. In the Ullmann reaction as well, the reaction has no selectivity, and hence not only the desired halogenated aminobiphenyl compound but also a diaminobiphenyl compound are simultaneously formed to make it unable to obtain the desired compound efficiently. Accordingly, it has been sought to provide a process for producing halogenated aromatic amine compounds efficiently.

Recently, a method developed by Buchwald or Hartwig et al. is also reported in which an arylhalide compound and an amine compound are allowed to react in the presence of a palladium catalyst to synthesize an arylamine compound efficiently (Tetrahedron Letters, Vol.36, No.21, p.3609, 1995; J. Am. Chem. Soc., V61.120, p.9772, 1998; J. Or. Chem., 61, p.1133, 1996). Syntheses in which this reaction is applied to the syntheses of dihalogenated biphenyl compounds are disclosed in Japanese Patent Applications Laid-open No. 11-21349 and No. 11-322679. In either of them, however, all halogen moieties of a dihalogenated biphenyl compound are aminated, and there is shown no example of synthesizing halogenated aminobiphenyl compounds.

SUMMARY OF THE INVENTION

An object of the present invention is to provide a process for producing a specific halogenated aromatic amine compound in a high selectivity and a high yield.

The present inventors have made extensive studies to settle the above subject. As the result, they have accomplished the present invention.

The present invention is a process for producing a halogenated aromatic amine compound, comprising allowing an aromatic amine compound represented by the following Formula (1):

$$H_2N\text{—}Ar^1 \quad (1)$$

wherein $Ar^1$ represents a substituted or unsubstituted monovalent aromatic hydrocarbon ring group or a substituted or unsubstituted monovalent aromatic heterocyclic ring group;

to react with a dihalogenated aromatic compound represented by the following Formula (2):

$$Y^1\text{—}Ar^2\text{—}Y^2 \quad (2)$$

wherein $Ar^2$ represents a substituted or unsubstituted divalent aromatic hydrocarbon ring group or a substituted or unsubstituted divalent aromatic heterocyclic ring group, and $Y^1$ and $Y^2$ each independently represent an iodine atom, a bromine atom or a chlorine atom;

in the presence of a metallic catalyst and a basic compound in a non-reactive solvent to obtain a halogenated aromatic amine compound represented by the following Formula (3):

wherein $Ar^1$, $Ar^2$ and $Y^1$ are as defined above;

the metallic catalyst being a catalyst having a phosphorus-containing ligand having at least one cyclic hydrocarbon group.

DESCRIPTION OF THE PREFERRED EMBODIMENTS

Where the halogenated aminobiphenyl compound is synthesized by the production process of the present invention, the desired compound is selectively obtained as shown by the following reaction scheme (A):

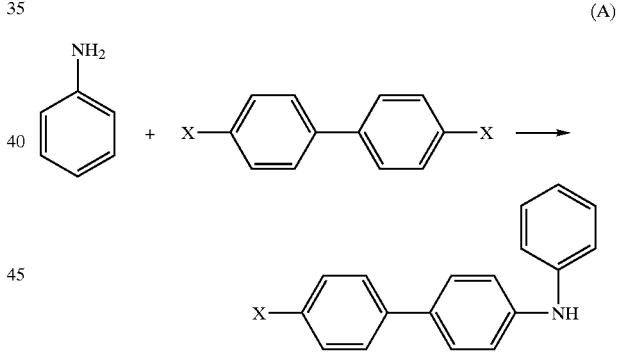

(A)

wherein X represents an iodine atom, a bromine atom or a chlorine atom.

However, where the compound is synthesized by the Ullmann process, not only the desired product is obtained, but also a product on both sides of the biphenyl of which have been aminated is obtained as a by-product, as shown by the following reaction scheme (B):

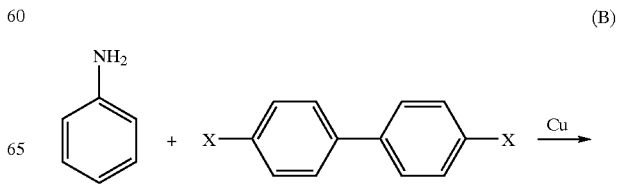

(B)

-continued

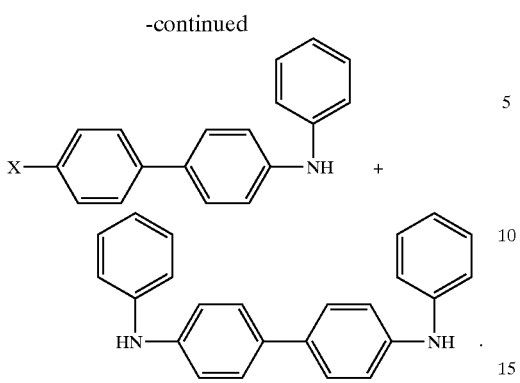

The reason why such a product on both sides of the biphenyl of which have been aminated is obtained has not been elucidated in detail, and it is presumed to be due to the fact that the Ullmann reaction requires high temperature (about 200° C.) and this makes the reaction have a low selectivity.

Where the halogenated aminobiphenyl compound is synthesized by the method developed by Buchwald or Hartwig et al. in which an arylamine compound is synthesized in the presence of a palladium catalyst and using tri(tert-butyl)phosphine disclosed in Japanese Patent Applications Laid-open No. 11-21349 and No. 11-322679, not only the desired product is obtained but also a product on both sides of the biphenyl of which have been aminated is obtained as a by-product. The reason therefor has not been elucidated in detail, and it is presumed to be due to the fact that the palladium catalyst and a metallic catalyst formed from the tri(tert-butyl)phosphine have so high reactivity that the selectivity of reaction has lowered, so that the product on both sides of the biphenyl of which have been aminated is obtained.

In the present invention, the, aromatic amine compound represented by Formula (1) is allowed to react with the dihalogenated aromatic compound represented by Formula (2) in the presence of i) a metallic catalyst having a phosphorus-containing ligand having at least one cyclic hydrocarbon group and ii) a basic compound in a non-reactive solvent to produce the halogenated aromatic amine compound represented by Formula (3). The high selectivity brought out by this process has not been elucidated in detail, but the following reasons may be given therefor. In the production process in the present invention, the reaction does not require so high temperature as that required in the Ullmann process, and hence this does not lower the selectivity of reaction. Also, the synthesis method developed by Buchwald or Hartwig et al. requires a ligand which feeds electric charges to the metallic catalyst. Thus, the flow of electric charges from the ligand into the metal is so large that the metallic catalyst may come to have electric charges in a high density, whereupon the oxidative addition reaction of an aromatic carbon/halogen bond on the metal, which corresponds to the first step of a catalyst cycle, is restrained when an electron-donative group is present on the aromatic group, as so presumed. It is considered that, at the stage where the halogen atom on one side of the dihalogenated aromatic compound has been aminated, the density of electric charges between the other halogen and the carbon is so high that the both-side halogen atoms are inhibited from being aminated together, and the selectivity is brought out such that only the halogen atom on one side is aminated. It, however, is considered that, where a trialkylphosphine, in which all the hydrogen atoms on the phosphorus have been substituted with alkyl groups, is used as a ligand of the metallic catalyst, the flow of electric charges into the central metal is so large as to make the rate of reaction very high to cause a lowering of selectivity.

In the present invention, the aromatic amine compound represented by Formula (1) may preferably be an aromatic amine compound represented by the following Formula (4):

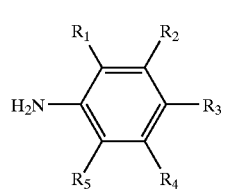

(4)

wherein $R_1$ to $R_5$ each independently represent a hydrogen atom, a substituted or unsubstituted alkyl group having any of 1 to 8 carbon atoms, a substituted or unsubstituted alkoxyl group having any of 1 to 8 carbon atoms, a substituted or unsubstituted aryl group, a substituted or unsubstituted aryl ether group, a fluorine atom, an alkyl fluoride group having any of 1 to 8 carbon atoms, a substituted or unsubstituted aryl thioether group, a substituted or unsubstituted pyridyl group, or a group represented by the following Formula (5):

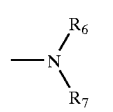

(5)

wherein $R_6$ and $R_7$ each independently represent a substituted or unsubstituted alkyl group or a substituted or unsubstituted aryl group.

Specific structural examples of the aromatic amine compound represented by Formula (1) in the present invention are shown below, but not particularly limited to these structures.

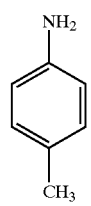

(1-1)

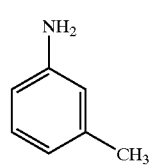

(1-2)

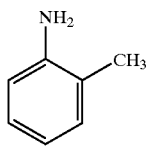 (1-3)
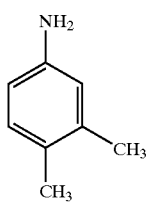 (1-4)
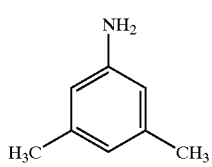 (1-5)
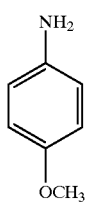 (1-6)
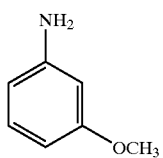 (1-7)
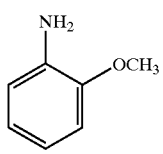 (1-8)
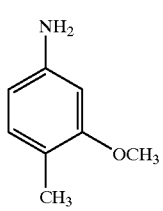 (1-9)
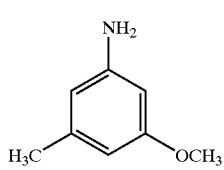 (1-10)
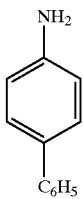 (1-11)
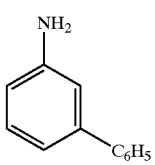 (1-12)
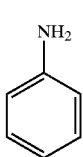 (1-13)
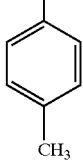 (1-14)
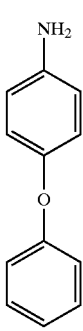 (1-14)
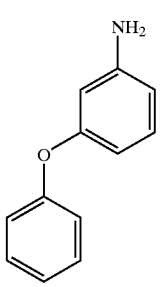 (1-15)
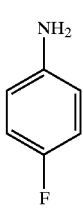 (1-16)

-continued
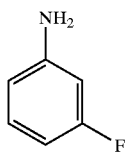 (1-17)
 (1-18)
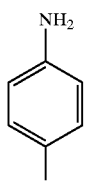 (1-19)
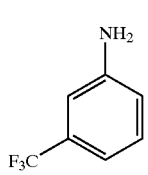 (1-20)
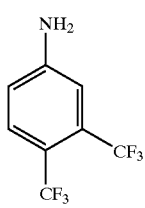 (1-21)
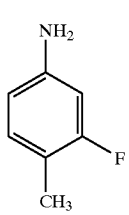 (1-22)
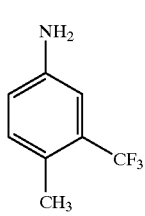 (1-23)
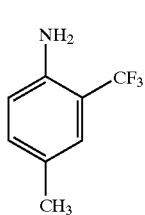 (1-24)
-continued
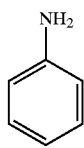 (1-25)
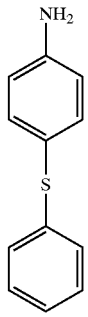 (1-26)
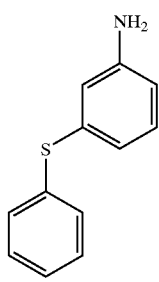 (1-27)
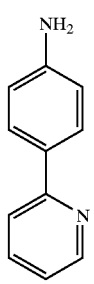 (1-28)
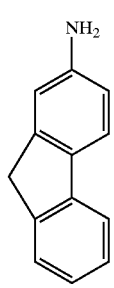 (1-29)
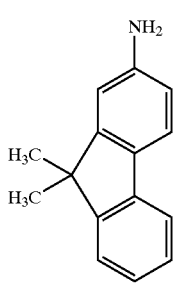 (1-30)

-continued
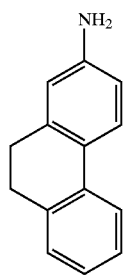 (1-31)
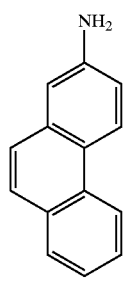 (1-32)
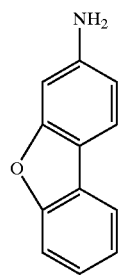 (1-33)
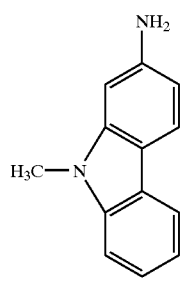 (1-34)
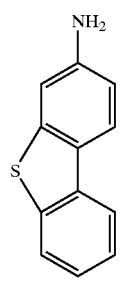 (1-35)
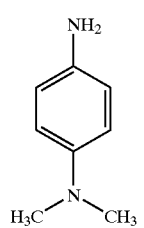 (1-36)
-continued
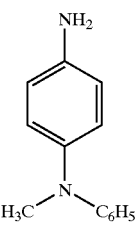 (1-37)
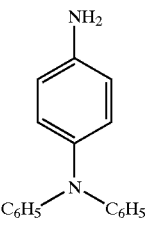 (1-38)
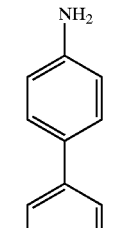 (1-39)
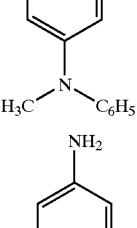 (1-40)
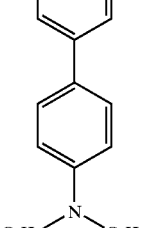 (1-41)
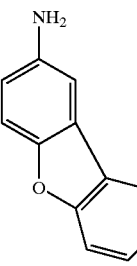 (1-42)
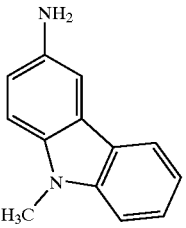

-continued (1-43)

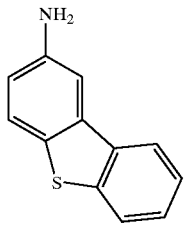

In the present invention, the dihalogenated aromatic compound represented by Formula (2) may preferably be a dihalogenated aromatic compound represented by the following Formula (6):

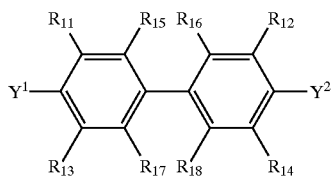

(6)

wherein $R_{11}$ to $R_{18}$ each independently represent a hydrogen atom, a substituted or unsubstituted alkyl group having any of 1 to 8 carbon atoms, a substituted or unsubstituted alkoxyl group having any of 1 to 8 carbon atoms, a substituted or unsubstituted aryl group, a substituted or unsubstituted aryl ether group, an alkyl fluoride group having any of 1 to 8 carbon atoms, a substituted or unsubstituted aryl thioether group or a substituted or unsubstituted pyridyl group; $R_{15}$ and $R_{16}$, and $R_{17}$ and $R_{18}$, may respectively independently combine through a carbon atom, a substituted or unsubstituted alkylene group, a substituted or unsubstituted alkylidene group, an oxygen atom, a nitrogen atom or a sulfur atom to form a condensed polycyclic structure or a heterocyclic structure; and $Y^1$ and $Y^2$ each independently represent an iodine atom, a bromine atom or a chlorine atom. The $Y^1$ and $Y^2$ in Formula (2) may also each preferably be a bromine atom.

Specific structural examples of the dihalogenated aromatic compound represented by Formula (2) in the present invention are shown below, but not particularly limited to these.

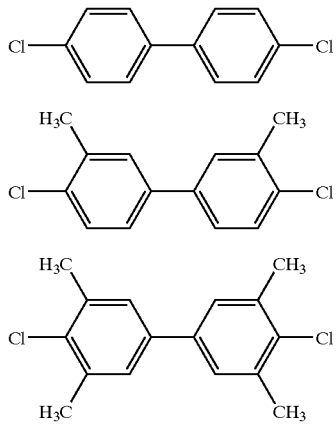

(2-1)

(2-2)

(2-3)

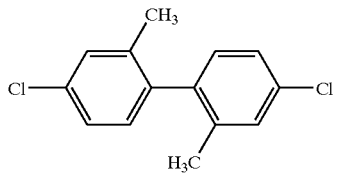

(2-4)

(2-5)

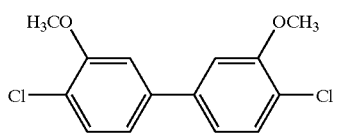

(2-6)

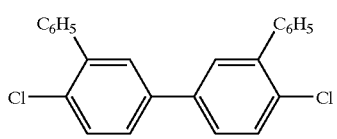

(2-7)

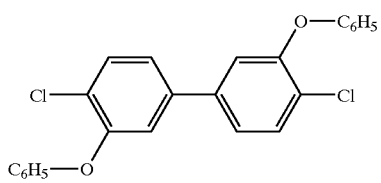

(2-8)

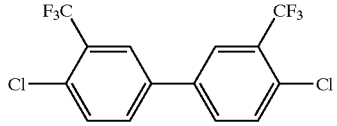

(2-9)

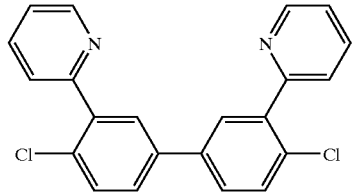

(2-10)

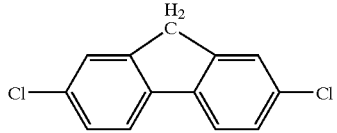

(2-11)

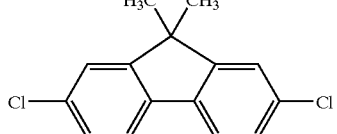

(2-12)

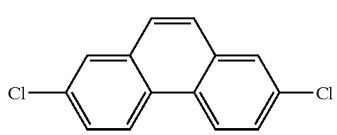

(2-13)

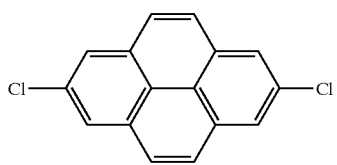

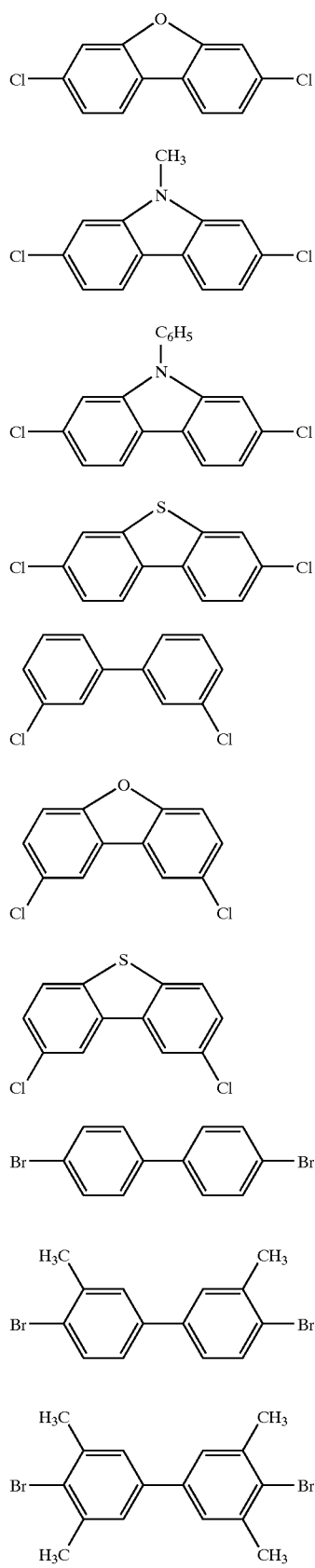
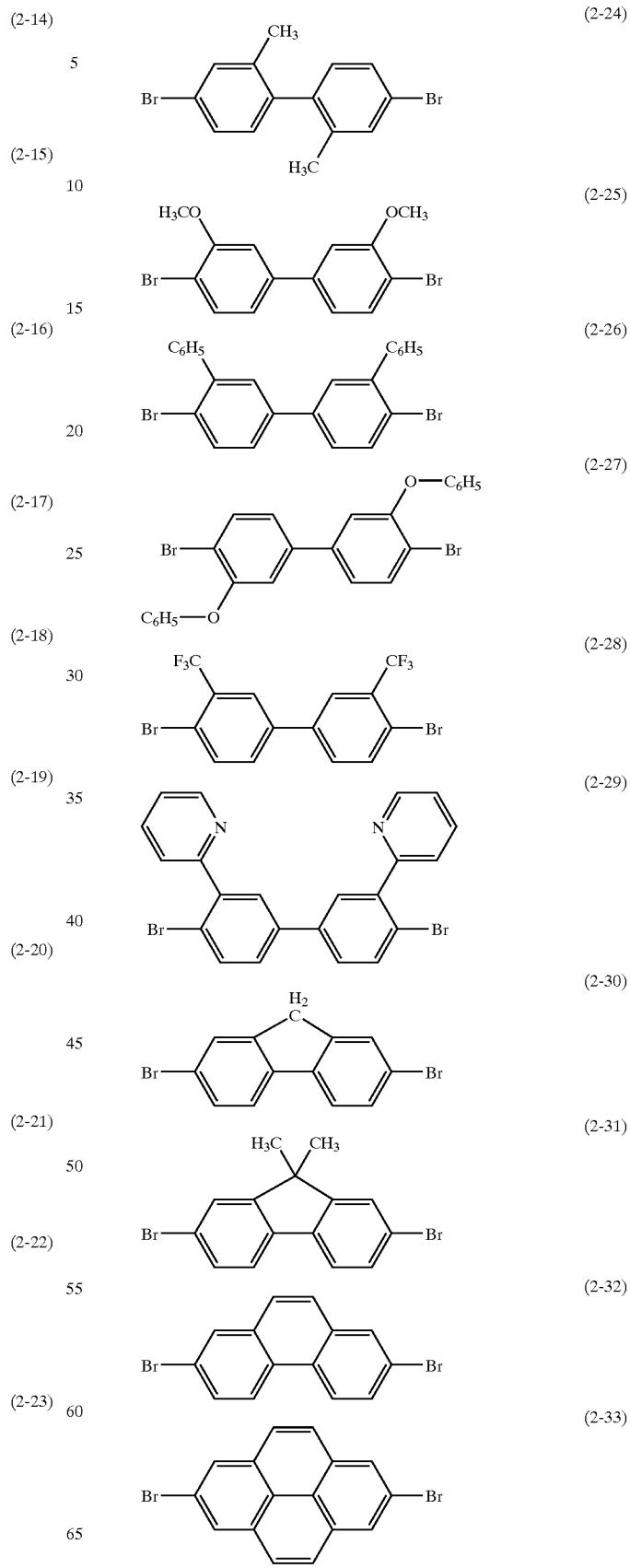

-continued
(2-34) 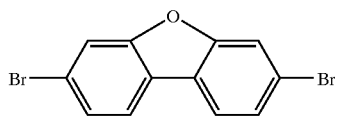
(2-35) 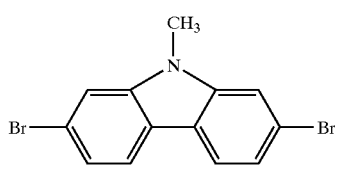
(2-36) 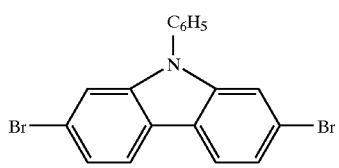
(2-37) 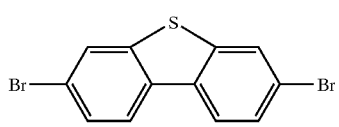
(2-38) 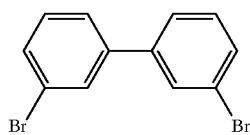
(2-39) 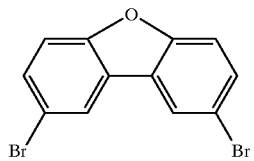
(2-40) 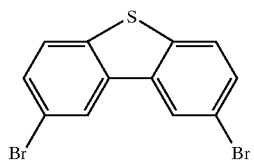
(2-41) 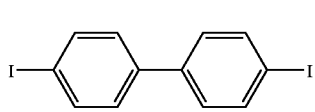
(2-42) 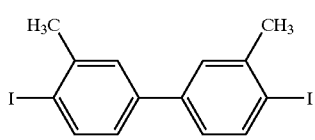
(2-43) 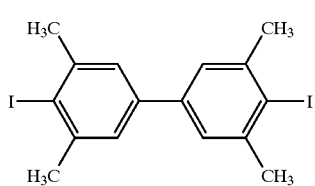
-continued
(2-44) 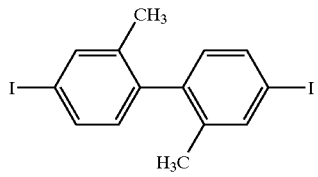
(2-45) 
(2-46) 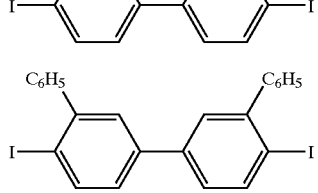
(2-47) 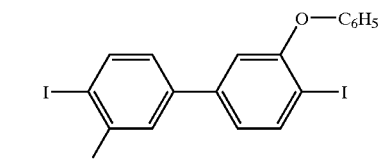
(2-48) 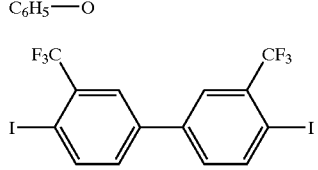
(2-49) 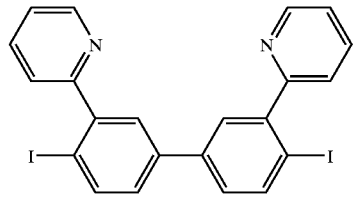
(2-50) 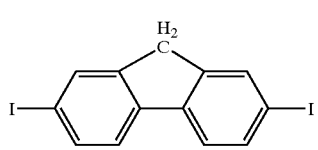
(2-51) 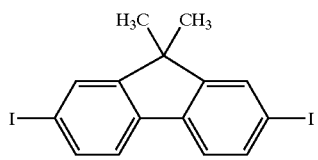
(2-52) 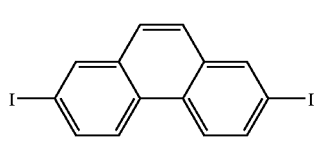
(2-53) 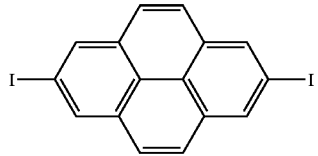

-continued (2-54)
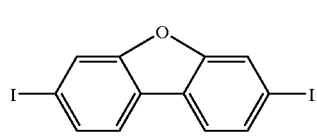

(2-55)
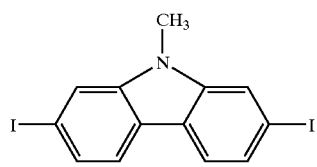

(2-56)
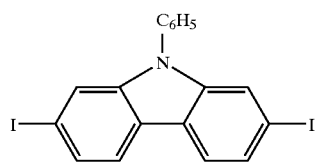

(2-57)
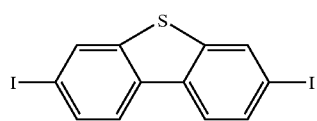

(2-58)
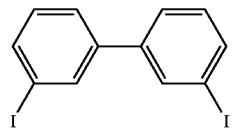

(2-59)
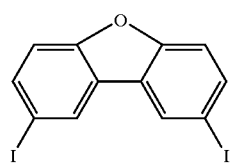

(2-60)
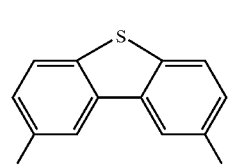

The dihalogenated aromatic compound represented by Formula (2) may preferably be used in an amount of from 1.0 time to 1.2 times in number of moles, based on the aromatic amine compound represented by Formula (1). It may more preferably be used in an amount of from 1.0 time to 1.1 times based on the aromatic amine compound represented by Formula (1).

In the present invention, the halogenated aromatic amine compound represented by Formula (3) may preferably be a halogenated aromatic amine compound represented by the following Formula (7):

(7)
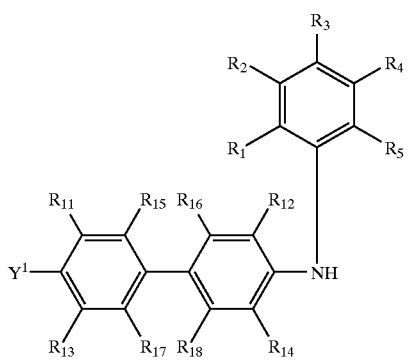

wherein $R_1$ to $R_5$, $R_{11}$ to $R_{18}$ and $Y^1$ are as defined previously.

Specific structural examples of the halogenated aromatic amine compound represented by Formula (3) in the present invention are shown below, but not particularly limited to these.

(3-1)
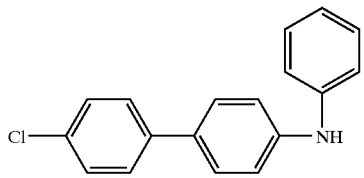

(3-2)
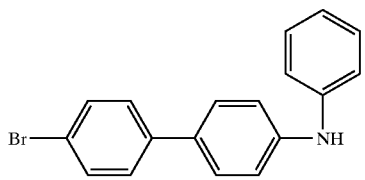

(3-3)
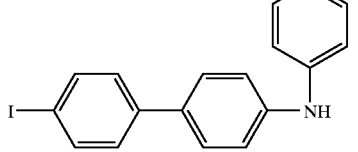

(3-4)
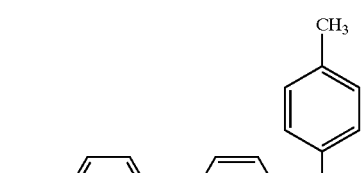

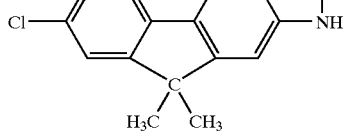

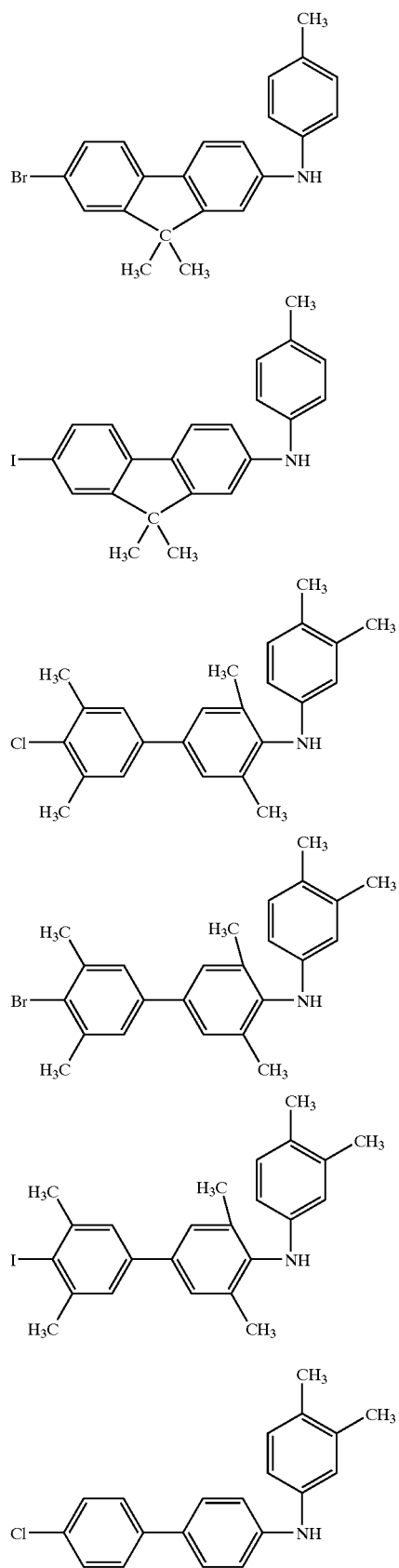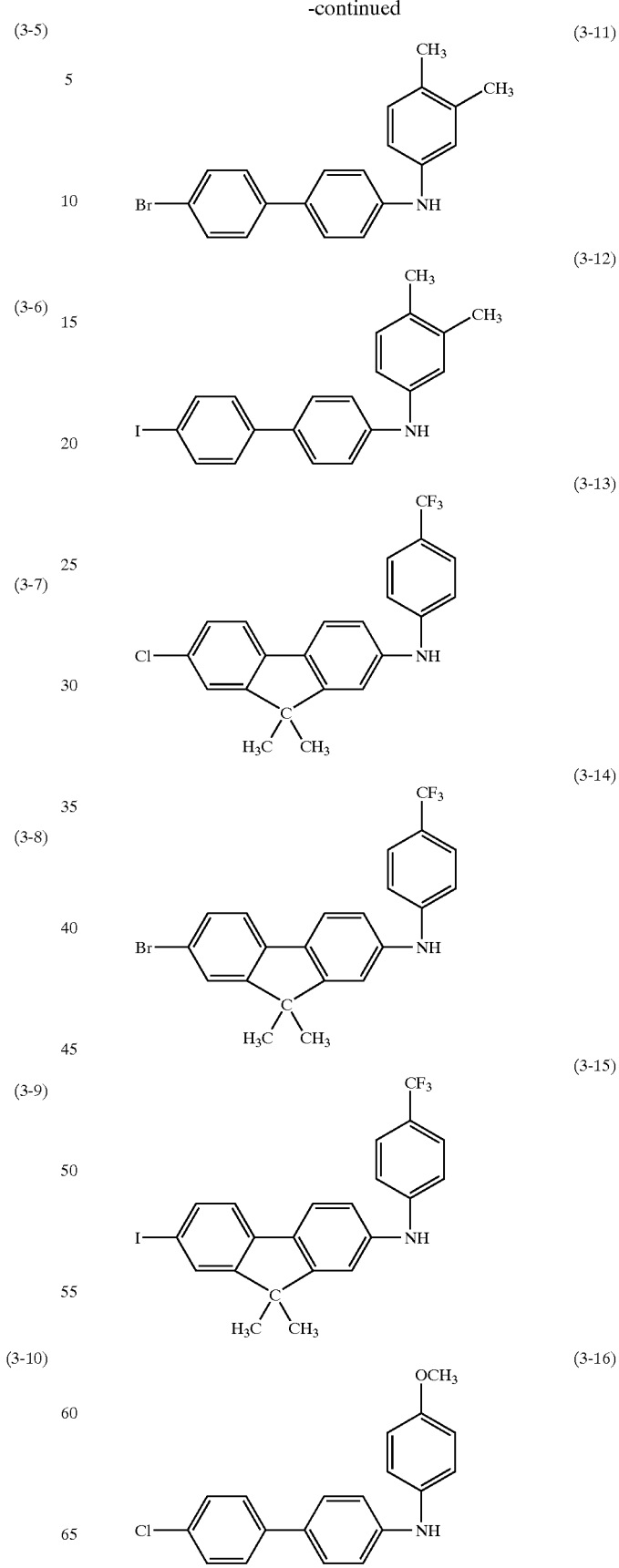

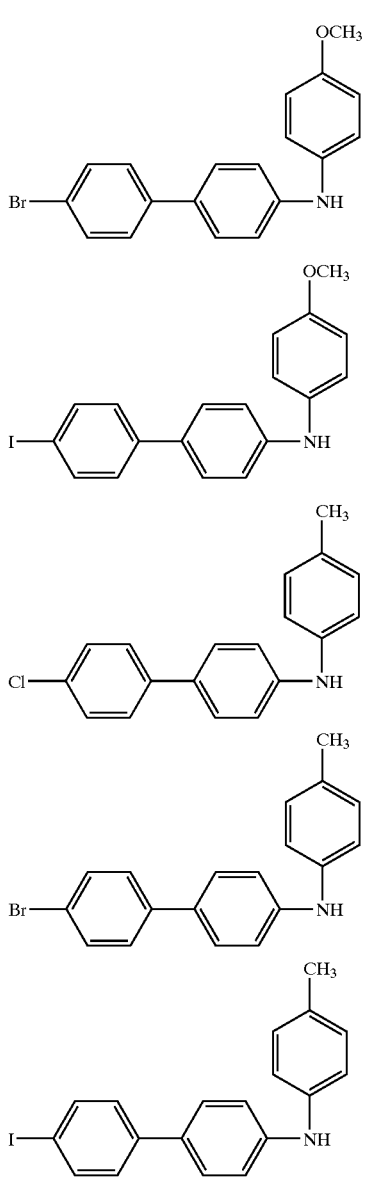

(3-17)

(3-18)

(3-19)

(3-20)

(3-21)

The metallic catalyst in the present invention may preferably be a palladium complex the center-forming metal atom of which is constituted of palladium or a nickel complex the center-forming metal atom of which is constituted of nickel. It may more preferably be a palladium complex constituting of palladium.

The metallic catalyst which acts on synthesis reaction may be either of a case in which it has already been prepared from a phosphorus-containing ligand and a metal outside the reaction system and a case in which a metallic catalyst having catalytic action is generated by making a metallic compound and a phosphorus-containing ligand present together inside the reaction system. In the latter case, the metallic compound may preferably be a palladium compound or a nickel compound, and may more preferably be a palladium compound, or a nickel compound, selected from the group consisting of $Pd(OAc)_2$, $Pd(Aca)_2$, $(CH_3CN)_2Pd(NO_2)Cl$, $(C_{10}H_8N_2)_2PdCl_2$, $Pd_2(dba)_3$, $PdCl_2$, $Ni(OAc)_2$, $Ni(Aca)_2$, $(CH_3CN)_2Ni(NO_2)Cl$, $(C_{10}H_8N_2)_2NiCl_2$, $Ni_2(dba)_3$ and $NiCl_2$.

The metallic catalyst may be used in an amount, but not particularly limited to, of from 0.0001 to 0.1 mole % in terms of the weight of the metallic catalyst, and more preferably from 0.002 to 0.08 mole % in terms of the weight of the metallic catalyst, based on the aromatic amine compound represented by Formula (1).

The phosphorus-containing ligand in the production process of the present invention may also preferably have at least one cyclic hydrocarbon group on a substituent on the phosphorus. The cyclic hydrocarbon group may also preferably be a substituted or unsubstituted phenyl group, a substituted or unsubstituted biphenyl group, a substituted or unsubstituted naphthyl group or a substituted or unsubstituted cyclopentadienyl group.

Specific structural examples of the phosphorus-containing ligand are shown below, but not particularly limited to these. In the following, "t-Bu" in structural examples represents tert-butyl.

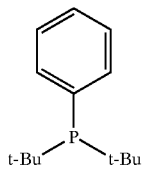

(6-1)

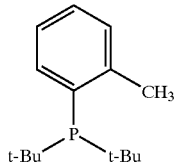

(6-2)

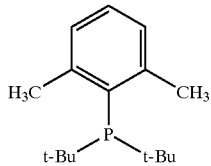

(6-3)

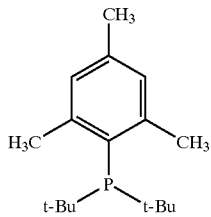

(6-4)

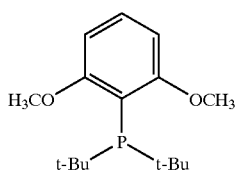

(6-5)

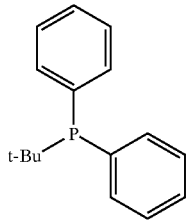

(6-6)

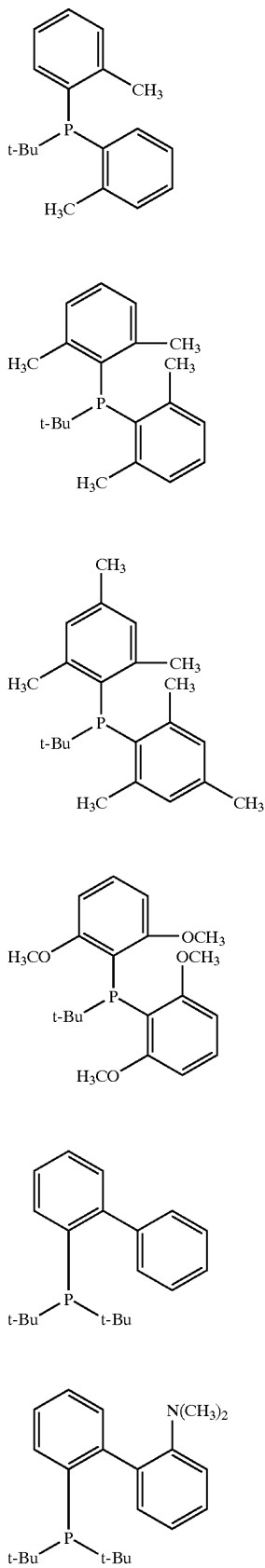
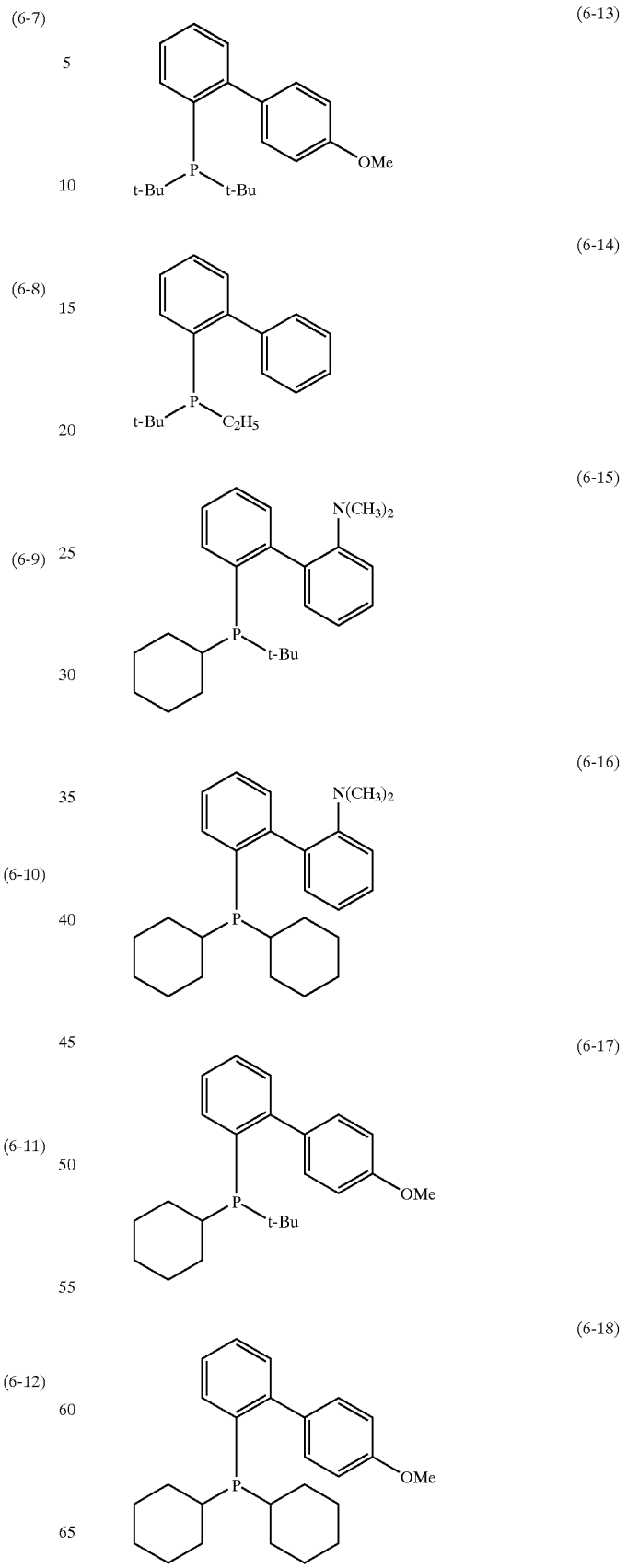

-continued
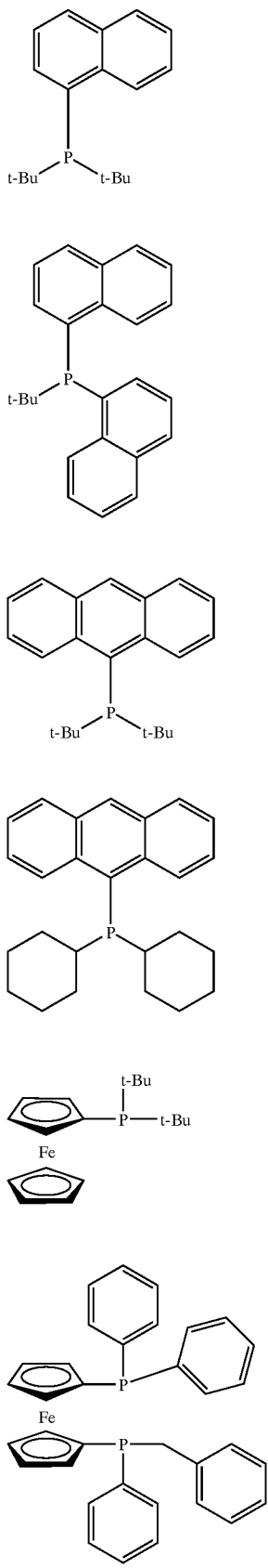
(6-19)
(6-20)
(6-21)
(6-22)
(6-23)
(6-24)
-continued
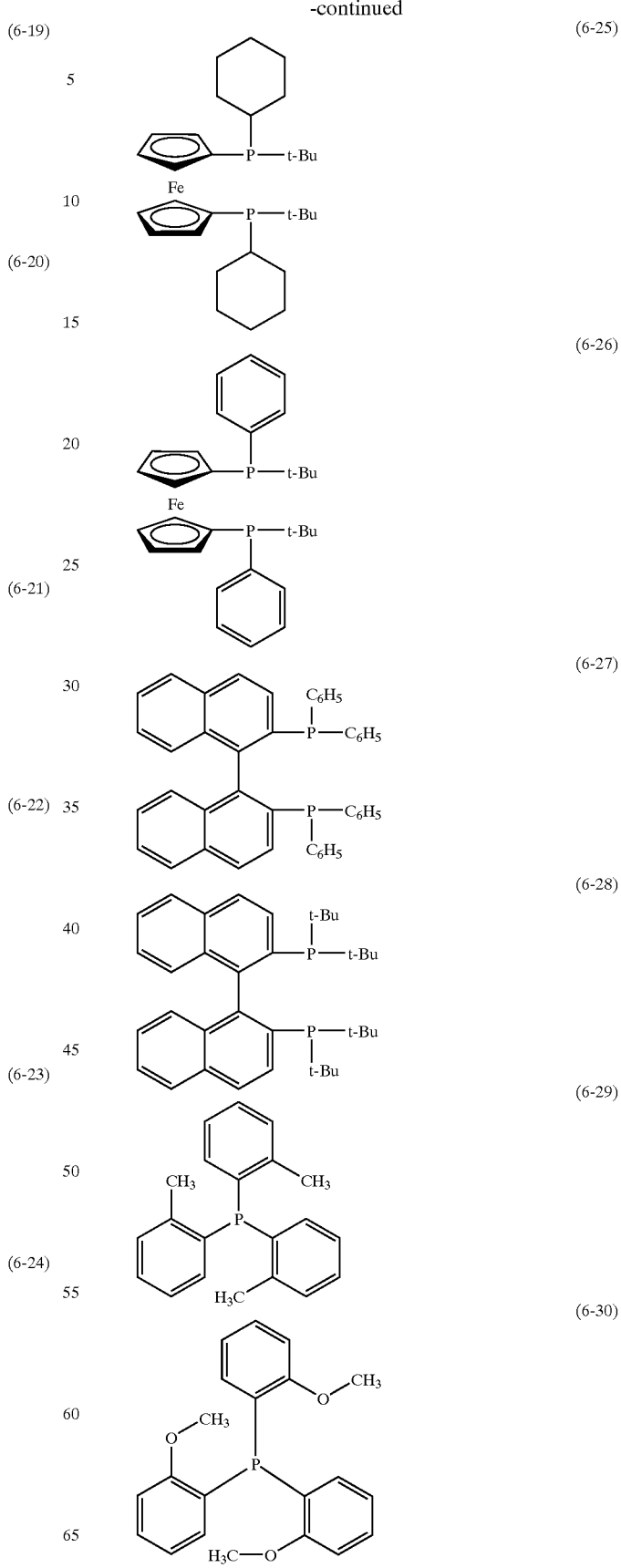
(6-25)
(6-26)
(6-27)
(6-28)
(6-29)
(6-30)

-continued

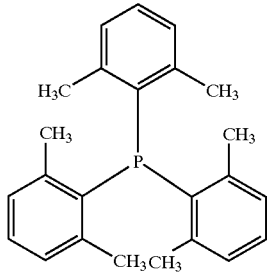
(6-31)

In regard to the amount in which the phosphorus compound is used, it may be, but not particularly limited to, 0.5 time to 10 times in number of moles, based on the metal in the catalyst, and more preferably 0.8 time to 5 times based on the metal in the catalyst.

The basic compound used in the present invention may preferably be a basic compound selected from the group consisting of an alkali metal alkoxide, an alkaline earth metal alkoxide, potassium carbonate and potassium tertiary phosphate. As examples of the alkali metal alkoxide, it may include lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide and potassium tert-butoxide. As examples of the alkaline earth metal alkoxide, it may include magnesium di(methoxide), magnesium di(ethoxide), magnesium di(isopropoxide) and magnesium di(potassium tert-butoxide).

As the solvent used in the present invention, there are no particular limitations as long as it is a non-reactive solvent that does not participate in the reaction of the present invention, like a halogen solvent. It may preferably be an aromatic hydrocarbon solvent such as benzene, toluene or xylene, or an ether type solvent such as monoglyme, diglyme, tetrahydrofuran or 1,4-dioxane.

In the present invention, the desired compound may be produced under normal pressure in air. In some cases, it may be produced in an atmosphere of inert gas such as nitrogen or argon. Still in some cases, reaction under pressure is feasible. At the time of production, the reaction may be carried out at a temperature between 50° C. and 200° C. From the viewpoint of selectivity, it may be carried out at a temperature of from 50° C. to 150° C. Reaction time may differ depending on the type and amount of raw materials used in the production, the type and amount of the metallic catalyst used, the type and amount of the phosphorus-containing ligand used, the type and amount of the basic compound used, the type of the solvent, and the reaction temperature. It may be selected within the range of from few minutes to 120 hours. From the viewpoint of selectivity, it is preferable for the reaction time to be as short as possible.

After the reaction has been completed, the reaction product may be treated by a conventional method to obtain the desired compound.

The present invention is described below by giving Examples. The present invention is by no means limited to these.

EXAMPLE 1

Into a three-necked flask of 200 ml in inner volume and fitted with a Dimroth type condenser, a thermometer and a stirrer, as an aromatic amine compound 4.65 g (0.05 mol) of aniline, represented by the above Formula (1-25), as a dihalogenated aromatic compound 15.6 g (0.05 mol) of 1-bromo-4-(4-bromophenyl)benzene, represented by the above Formula (2-21), as a metallic compound used in a metallic catalyst 20.112 g (0.0005 mol) of Pd(OAc), as a phosphorus-containing ligand 0.60 g (4 times in number of moles, based on the metal) of the compound represented by Formula (6-11), as a basic compound 5.6 g (0.07 mol) of sodium tert-butoxide, as an internal standard 100 mg of terphenyl and as a solvent 90 ml of toluene were introduced. Thereafter, these were heated in an oil bath to temperature at which the toluene continued reflux, and then stirred for 3 hours to carry out reaction. Thereafter, the reaction mixture was left to cool to room temperature. After the reaction mixture cooled to room temperature, this was neutralized with hydrochloric acid water, and the organic layer was quantitatively analyzed by gas chromatography (HP6890, manufactured by Hewlett Packard Co.) to measure the yield of the desired halogenated aromatic amine compound shown in Table 1. The results are shown in Table 1.

EXAMPLES 2 & 3

In Example 1, the aromatic amine compound, the dihalogenated aromatic compound, the metallic compound used in a metallic catalyst and the phosphorus-containing ligand were changed as shown in Table 1, to carry out reaction and quantitative analysis to measure the yield of the desired halogenated aromatic amine compound shown in Table 1. The results are shown in Table 1.

EXAMPLES 4 to 6

In Example 1, the aromatic amine compound, the dihalogenated aromatic compound, the metallic compound used in a metallic catalyst and the phosphorus-containing ligand were changed as shown in Table 1 and the solvent was changed to 1,4-dioxane, to carry out reaction and quantitative analysis to measure the yield of the desired halogenated aromatic amine compound shown in Table 1. The results are shown in Table 1.

EXAMPLES 7 & 8

In Example 1, the aromatic amine compound, the dihalogenated aromatic compound, the metallic compound used in a metallic catalyst and the phosphorus-containing ligand were changed as shown in Table 1 and the solvent was changed to diglyme, to carry out reaction and quantitative analysis to measure the yield of the desired halogenated aromatic amine compound shown in Table 1. The results are shown in Table 1.

Comparative Example 1

Into a three-necked flask of 200 ml in inner volume and fitted with a condenser, a thermometer and a stirrer, as an aromatic amine compound 4.65 g (0.05 mol) of aniline, represented by the above Formula (1-25), as a dihalogenated aromatic compound 20.3 g (0.05 mol) of 1-iodo-4-(4-iodophenyl)benzene, represented by the above Formula (2-41), 9.6 g (0.15 mol) of copper powder, as an internal standard 100 mg of terphenyl and as a solvent 90 ml of o-dichlorobenzene were introduced. Thereafter, these were heated in an oil bath to 200° C., and then stirred for 6 hours to carry out reaction. Thereafter, the reaction mixture was left to cool to room temperature. After the reaction mixture cooled to room temperature, the organic layer was quantitatively analyzed by gas chromatography to measure the yield of the halogenated aromatic amine compound shown in Table 1. The results are shown in Table 1.

Comparative Example 2

Into a three-necked flask of 200 ml in inner volume and fitted with a Dimroth type condenser, a thermometer and a stirrer, as an aromatic amine compound 4.65 g (0.05 mol) of aniline, represented by the above Formula (1-25), as a dihalogenated aromatic compound 15.6 g (0.05 mol) of 1-bromo-4-(4-bromophenyl)benzene, represented by the above Formula (2-21), as a metallic compound used in a metallic catalyst 20.112 g (0.0005 mol) of Pd(OAc), as a phosphorus-containing ligand 0.40 g (4 times in number of moles, based on the metal) of tri(tert-butyl)phosphine, represented by the following Formula (8), as a basic compound 5.6 g (0.07 mol) of sodium tert-butoxide, as an internal standard 100 mg of terphenyl and as a solvent 90 ml of toluene were introduced. Thereafter, these were heated in an oil bath to temperature at which the toluene continued reflux, and then stirred for 3 hours to carry out reaction. Thereafter, the reaction mixture was left to cool to room temperature. After the reaction mixture cooled to room temperature, this was neutralized with hydrochloric acid water, and the organic layer was quantitatively analyzed by gas chromatography to measure the yield of the halogenated aromatic amine compound shown in Table 1. The results are shown in Table 1.

intermediate of coloring matters such as organic dyes and pigments, and also an intermediate of organoelectroluminescence materials, and an intermediate of photosensitive materials or organic conductor materials of organic photosensitive members in electrophotography.

The present invention makes it possible to provide a production process in which the halogenated aromatic amine compound, which has ever been difficult to produce, is produced in a high selectivity and a high yield from the aromatic amine compound and dihalogenated aromatic compound, by using i) the metallic catalyst having a phosphorus-containing ligand having at least one cyclic hydrocarbon group and ii) the basic compound.

What is claimed is:

1. A process for producing a halogenated aromatic amine compound, comprising allowing an aromatic amine compound represented by the following Formula (1): $H_2N\text{—}Ar^1$ (1), wherein $Ar^1$ represents a substituted or unsubstituted phenyl group, to react with a dihalogenated aromatic compound represented by the following Formula (2): $Y^1\text{—}Ar^2\text{—}Y^2$ (2), wherein $Ar^2$ represents a substituted or unsubstituted biphenylene group or a substituted or unsubstituted fluorenylene group, and $Y^1$ and $Y^2$ each independently represent an iodine atom, a bromine atom or a chlorine atom, in the presence of a metallic catalyst and a basic compound in a non-reactive solvent to obtain a halogenated aromatic amine compound represented by the following Formula (3):

TABLE 1

(8)

$$t\text{-Bu}\text{—}P(\text{-}t\text{-Bu})\text{—}t\text{-Bu}$$

| | Aromatic amine compound | Dihalogenated aromatic compound | Metallic compound | Phosphorus = containing ligand | Basic compound | Halogenated aromatic amine compound | Yield |
|---|---|---|---|---|---|---|---|
| Example: | | | | | | | |
| 1 | 1-25 | 2-21 | Pd(OAc)$_2$ | 6-11 | sodium tert-butoxide | 3-2 | 83% |
| 2 | 1-1 | 2-51 | PdCl$_2$ | 6-10 | sodium tert-butoxide | 3-6 | 74% |
| 3 | 1-4 | 2-23 | Pd$_2$(dba)$_3$ | 6-31 | sodium tert-butoxide | 3-8 | 78% |
| 4 | 1-4 | 2-21 | Pd(OAc)$_2$ | 6-24 | sodium tert-butoxide | 3-11 | 94% |
| 5 | 1-19 | 2-31 | PdCl$_2$ | 6-25 | sodium tert-butoxide | 3-14 | 92% |
| 6 | 1-6 | 2-41 | Pd$_2$(dba)$_3$ | 6-23 | sodium tert-butoxide | 3-18 | 84% |
| 7 | 1-4 | 2-41 | NiCl$_2$ | 6-24 | sodium tert-butoxide | 3-12 | 78% |
| 8 | 1-1 | 2-41 | NiCl$_2$ | 6-26 | sodium tert-butoxide | 3-21 | 72% |
| Comparative Example: | | | | | | | |
| 1 | 1-25 | 2-41 | copper powder | — | — | 3-3 | 59% |
| 2 | 1-25 | 2-21 | Pd(OAc)$_2$ | 8 | sodium tert-butoxide | 3-2 | 53% |

In Examples, the halogenated aminobiphenyl has been obtained in a good yield in all cases. However, in the conventional case Comparative Example 1 (Ullmann process) or in the case when tri(tert-butyl)phosphine is used as the phosphorus-containing ligand, the reaction has a low selectivity, resulting in a low yield of the compound obtained.

As described above, the utility of the present invention has been demonstrated as a process for synthesizing the halogenated aminobiphenyl compound useful as an intermediate of pharmaceuticals and agricultural chemicals, an genated aromatic amine compound represented by the following Formula (3):

(3)

$$Y^1\text{—}Ar^2\text{—}\underset{\underset{H}{|}}{N}\text{—}Ar^1$$

wherein $Ar^1$, $Ar^2$ and $Y^1$ are as defined above, wherein the metallic catalyst has a phosphorus-containing ligand having at least one cyclic hydrocarbon group, and wherein the phosphorus-containing ligand is represented by formula (6-10), (6-11), (6-23), (6-24), (6-25), (6-26) or (6-31):

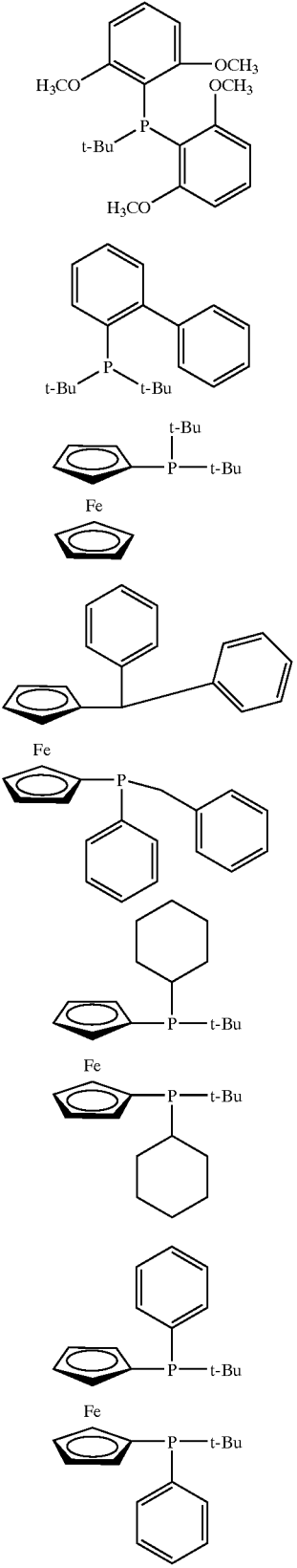

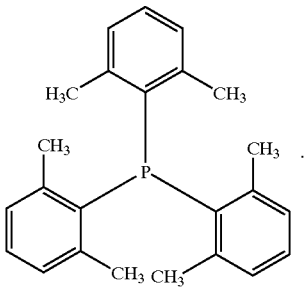

2. The process for producing a halogenated aromatic amine compound according to claim 1, wherein said aromatic amine compound represented by Formula (1) is an aromatic amine compound represented by the following Formula (4):

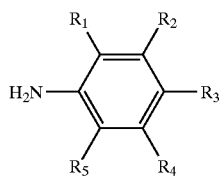

wherein $R_1$ to $R_5$ each independently represent a hydrogen atom, a substituted or unsubstituted alkyl group having any of 1 to 8 carbon atoms, a substituted or unsubstituted alkoxyl group having any of 1 to 8 carbon atoms, a substituted or unsubstituted aryl group, a substituted or unsubstituted aryl ether group, a fluorine atom, an alkyl fluoride group having any of 1 to 8 carbon atoms, a substituted or unsubstituted aryl thioether group, a substituted or unsubstituted pyridyl group, or a group represented by the following Formula (5):

wherein $R_6$ and $R_7$ each independently represent a substituted or unsubstituted alkyl group or a substituted or unsubstituted aryl group.

3. The process for producing a halogenated aromatic amine compound according to claim 1, wherein said dihalogenated aromatic compound represented by Formula (2) is a dihalogenated aromatic compound represented by the following Formula (6):

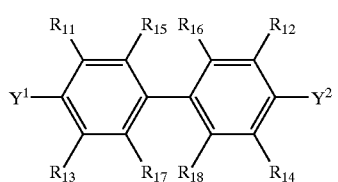

wherein $R_{11}$ to $R_{18}$ each independently represent a hydrogen atom, a substituted or unsubstituted alkyl group having any of 1 to 8 carbon atoms, a substituted or unsubstituted alkoxyl group having any of 1 to 8 carbon atoms, a substituted or unsubstituted aryl group, a substituted or unsubstituted aryl ether group, an alkyl fluoride group having any of 1 to 8 carbon atoms, a substituted or unsubstituted aryl thioether group or a substituted or unsubstituted pyridyl group; $R_{15}$ and $R_{16}$, and $R_{17}$ and $R_{18}$, may respectively independently combine through a carbon atom, a substituted or unsubstituted alkylene group, a substituted or unsubstituted alkylidene group, an oxygen atom, a nitrogen atom or a sulfur atom to form a condensed polycyclic structure or a heterocyclic structure; and $Y^1$ and $Y^2$ each independently represent an iodine atom, a bromine atom or a chlorine atom.

4. The process for producing a halogenated aromatic amine compound according to claim 1, wherein said metallic catalyst is either of a palladium complex and a nickel complex which have at least one cyclic hydrocarbon group on a substituent on the phosphorus.

5. The process for producing a halogenated aromatic amine compound according to claim 1, wherein said cyclic hydrocarbon group is a substituted or unsubstituted phenyl group, a substituted or unsubstituted biphenyl group, a substituted or unsubstituted naphthyl group or a substituted or unsubstituted cyclopentadienyl group.

6. The process for producing a halogenated aromatic amine compound according to claim 1, wherein said metallic catalyst is a complex produced from a palladium complex or a nickel complex and a phosphorus-containing ligand having at least one cyclic hydrocarbon group, inside the reaction system during said reaction.

7. The process for producing a halogenated aromatic amine compound according to claim 6, wherein said palladium complex or nickel complex is selected from the group consisting of $Pd(OAc)_2$, $Pd(Aca)_2$, $(CH_3CN)_2Pd(NO_2)Cl$, $(C_{10}H_8N_2)_2PdCl_2$, $Pd_2(dba)_3$, $PdCl_2$, $Ni(OAc)_2$, $Ni(Aca)_2$, $(CH_3CN)_2Ni(NO_2)Cl$, $(C_{10}H_8N_2)_2NiCl_2$, $Ni_2(dba)_3$ and $NiCl_2$.

8. The process for producing a halogenated aromatic amine compound according to claim 1, wherein said basic compound is selected from the group consisting of an alkali metal alkoxide, an alkaline earth metal alkoxide, potassium carbonate and potassium tertiary phosphate.

9. The process for producing a halogenated aromatic amine compound according to claim 1, wherein said $Y^1$ and $Y^2$ in Formulas (2) and (3) are each a bromine atom.

10. The process for producing a halogenated aromatic amine compound according to claim 1, wherein the reaction is carried out at a temperature of from 50° C. to 150° C.

* * * * *

UNITED STATES PATENT AND TRADEMARK OFFICE
CERTIFICATE OF CORRECTION

PATENT NO. : 7,009,080 B2
APPLICATION NO. : 10/671674
DATED : March 7, 2006
INVENTOR(S) : Harunobu Ogaki et al.

It is certified that error appears in the above-identified patent and that said Letters Patent is hereby corrected as shown below:

ON TITLE PAGE AT (56) OTHER PUBLICATIONS, col. 2;

After "David W. Old et al.,": "Animation" should read --Amination--.

COLUMN 1

Line 26, "(1983)." should read --(1983)).--; and
Line 42, "V61. 120," should read --Vol. 120,--.

COLUMN 3

Line 34, "so" should read --such a--; and
Line 50, "so" should read --such a--.

COLUMN 30,

Line 9, "ever" should read --always--.

COLUMN 31

Lines 28-33, " 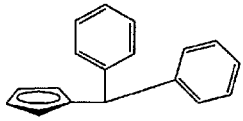 " should read -- 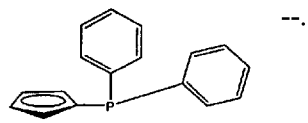 --.

UNITED STATES PATENT AND TRADEMARK OFFICE
CERTIFICATE OF CORRECTION

PATENT NO. : 7,009,080 B2
APPLICATION NO. : 10/671674
DATED : March 7, 2006
INVENTOR(S) : Harunobu Ogaki et al.

It is certified that error appears in the above-identified patent and that said Letters Patent is hereby corrected as shown below:

COLUMN 33

Line 20, "either of a palladium complex and" should read --a palladium complex or--; and
Line 21, "which have" should read --, which has--.

Signed and Sealed this

Seventeenth Day of October, 2006

JON W. DUDAS
*Director of the United States Patent and Trademark Office*